United States Patent [19]

Dorman

[11] 4,421,896
[45] Dec. 20, 1983

[54] METHOD OF COUPLING A PROTEIN TO A POLYMER PARTICLE CONTAINING HYDRAZIDE GROUPS IN A POLYMER LATEX AND THE PRODUCTS FORMED THEREFROM

[75] Inventor: Linneaus C. Dorman, Midland, Mich.

[73] Assignee: The Dow Chemical Company, Midland, Mich.

[21] Appl. No.: 349,557

[22] Filed: Feb. 17, 1982

Related U.S. Application Data

[63] Continuation-in-part of Ser. No. 93,409, Nov. 13, 1979, abandoned.

[51] Int. Cl.³ .............................................. C08L 89/00
[52] U.S. Cl. .................................... 525/54.1; 435/181
[58] Field of Search ..................... 525/54.1, 154, 376; 435/181

[56] References Cited

U.S. PATENT DOCUMENTS

| | | | |
|---|---|---|---|
| 3,234,096 | 2/1966 | Pollack | 167/84.5 |
| 3,309,275 | 3/1967 | Treacy | 167/84.5 |
| 3,514,429 | 5/1970 | Stahmann et al. | 260/80.73 |
| 3,619,371 | 11/1971 | Crook et al. | 195/63 R |
| 3,666,733 | 5/1972 | Epton | 260/80.3 N |
| 3,764,477 | 10/1973 | Lehmann et al. | 195/63 |
| 3,847,745 | 11/1974 | Axen et al. | 195/68 |
| 3,853,987 | 12/1974 | Dreyer | 424/1 |
| 3,857,931 | 12/1974 | Hager | 424/12 |
| 3,959,080 | 5/1976 | Orth et al. | 195/63 |
| 4,001,583 | 1/1977 | Barrett | 250/303 |
| 4,045,384 | 8/1977 | Dorman | 260/8 |
| 4,046,723 | 9/1977 | Dorman | 260/8 |
| 4,094,841 | 6/1978 | Mani | 260/29.6 H |
| 4,115,305 | 9/1978 | Hornby | 525/54.1 |
| 4,118,349 | 10/1978 | Bonacker et al. | 260/8 |
| 4,140,662 | 2/1979 | Reckel et al. | 260/8 |
| 4,181,636 | 1/1980 | Fischer | 260/8 |
| 4,210,723 | 7/1980 | Dorman | 435/180 |
| 4,264,766 | 4/1981 | Fischer | 536/51 |
| 4,266,030 | 5/1981 | Tschang et al. | 435/180 |
| 4,278,651 | 7/1981 | Hales | 424/1 |
| 4,279,787 | 7/1981 | Huizinga | 260/8 |

FOREIGN PATENT DOCUMENTS

| | | |
|---|---|---|
| 845402 | 8/1976 | Belgium . |
| 2530247 | 1/1976 | Fed. Rep. of Germany . |
| 2840768 | 3/1979 | Fed. Rep. of Germany . |
| 554867 | 5/1977 | U.S.S.R. . |

OTHER PUBLICATIONS

Inman et al.,–"the Derivatization of Crosslinked Polyacrylamide Beads, Controlled Introduction of Functional Groups for Preparation of Special Purpose, Biochemical Adsorbents"–Biochemistry vol. 8, No. 10 (1969) pp. 4074-4082.

Means and Feeny–"Chemical Modification of Poteins, (1971) pp. 165-174.

J. Sri Ram–"Preparation of Protein Conjugates and some Novel Polyamino Acid Derivatives Employing a Bifunctional Reagent"–Biochim. Biophys. Acta 78(1963) 228-230.

Quash et al.–"The Preparation of Latex Particles with Co-Valently Bound Polyamines, IgG and Measles Agglutinins and Their Use in Visual Agglutination Tests'"–Journal of Immunlogical Methods, 22 (1978) 165-174.

Primary Examiner—Veronica P. Hoke

[57] ABSTRACT

The invention describes a polymer particle-protein conjugate and the method of its preparation utilizing polymer particles having reactive surface hydrazide groups and a difunctional compound to bind the protein to the polymer particles in a polymer latex. Products derived from the invention can be used in latex agglutination tests for the detection of pregnancy or for the detection of proteins which may be indicative of disease states.

12 Claims, No Drawings

METHOD OF COUPLING A PROTEIN TO A POLYMER PARTICLE CONTAINING HYDRAZIDE GROUPS IN A POLYMER LATEX AND THE PRODUCTS FORMED THEREFROM

CROSS-REFERENCE TO RELATED U.S. APPLICATION

This Application is a continuation-in-part of copending U.S. application Ser. No. 093,409 filed Nov. 13, 1979, abandoned.

BACKGROUND OF THE INVENTION

The antigen-antibody reaction is the basis for all immunological test methods. Special proteins called antibodies are produced by an animal in response to the presence of an antigen, that is a foreign protein, in the body fluids of the animal. This normal body response to a foreign protein has led to the development of a number of techniques which are used to diagnose various human and animal diseases or disorders. Immunological test methods may also be used to detect pregnancy. In vitro tests for the presence of a suspected antigen or antibody in a body fluid are carried out by adding the immunological counterpart to a vial of the body fluid, i.e. add antigen if the test is for the presence of antibody or add antibody if the test is for the presence of antigen. If the suspected protein is present the resulting antigen-antibody reaction is generally indicated by precipitation or agglutination of the antigen-antibody complex. As used herein the term body fluid refers to urine, serum, plasma, or the like.

In some instances the antigen-antibody complex is slow to form and the particles that are formed are too small to be observed with certainty. In such cases, detectability of the antigen-antibody reaction can be improved by utilizing a carrier. When the antigen or antibody is coated on the surface of a carrier the reaction with the immunological counterpart produces a visible mass or agglutant. The proteinic antigen or antibody may be adsorbed onto the surface of carriers such as erythrocytes, bacterial cells, bentonite, polystyrene latex particles, anionic phenolic resins, or finely divided diazotized amino cellulose. It has been found however, that chemical binding of the antigen or antibody molecule to the carrier is superior to physical adsorption.

Immunological test methods for proteins such as human chorionic gonadotropin (HCG) and myoglobin may be useful as an aid in medical diagnosis.

A number of immunological tests have been developed for the detection of HCG in urine or serum. HCG is a glycoprotein with a molecular weight of about 27,000 produced by the chorionic tissue of the placenta during pregnancy, Systems using HCG have been used to detect pregnancy. During pregnancy this hormone governs the production and secretion of progesterone by the corpus luteum. HCG is also produced in large quantities by hydatidiform moles, choriocarcinomas, and some tumors of the tests. Low levels of HCG have also been found by radioimmunoassay in the sera of patients with various nontrophoblastic neoplasms. Various agglutination techniques have been used to test for the presence of HCG.

Agglutination testing for HCG may be performed by either the indirect or the direct technique. In the indirect technique the clinical sample is mixed with HCG antibody at a dilution that will be completely bound by one or more International Units/Milliliter (I.U./ML) of HCG. After an initial incubation period an indicator system consisting of HCG bound to a particulate carrier (latex or red cells) is added to the mixture. If HCG is present in the clinical sample the HCG antibody will not be available to react with the HCG-carrier complex and there will be no agglutination, thus, absence of agglutination is a positive test for HCG. If, on the other hand, HCG is not present in the clinical sample the HCG antibody will react with the HCG-carrier complex causing agglutination of the indicator system. This is a negative test for HCG in the clinical sample. In the direct technique HCG antibody bound to the carrier reacts directly with the HCG in the clinical sample and there is no need for an intermediate incubation step. Thus, in the direct technique agglutination indicates a positive test for HCG in the clinical sample.

Myoglobin is a muscle protein resembling hemoglobin in that myoglobin can reversibly bind oxygen. The concentration of cardiac myoglobin has been found to be increased in serum and urine after myocardial infarction. This increase in myoglobin concentration has been used as a diagnostic indicator of acute myocardial infarction. Increased levels of myoglobin can be detected hours before the elevation of cardiac enzymes thus serving as an early aid to diagnosis. The greatest levels of urinary myoglobin appear within hours of onset of clinical symptoms. Urinary myoglobin is a specific and sensitive diagnostic indicator of serious renal and respiratory failure as well, Hibrawi, H. and R. G. Blaker, Clin. Chem. 21/6:765 (1975), and methods of measurement have included radioimmunoassay, immunofluorescence, radial immunodiffusion, complement fixation, counterimmunoelectrophoresis and hemagglutination tests. All of these methods incorporate the use of an antibody derived from immunizing animals with a human myoglobin preparation.

It would be highly desirable to provide an effective, easy to read diagnostic test for the detection of particular proteins.

The prior art teaches that polyacrylamide can be functionalized by treatment with glutaraldehyde to which ligands bearing amino groups may be bound as Schiff's bases, Ternynck, et al., F.E.B.S. Letters, 23, 24 (1972). The present invention utilizes the hydrazide group which is more nucleophilic than the primary amide group, therefore the reactions of hydrazides, as embodied in this invention, can be carried out with greater ease under milder conditions and with a larger variety of functional groups. When working with a water-based colloid, such as a latex, this greater reactivity is a substantial advantage.

The prior art also teaches that amino-bearing bodies such as peptides and proteins can be attached chemically to polymeric water-insoluble carriers bearing hydrazine residues via dialdehydes, German (West) Patent DT No. 2,530,247 (1976). These water insoluble carriers include agarose polymer, acrylamide, polyethylene/maleic anhydride polymer, cellulose, a substituted cellulose, polyamide and glass. It is physically possible to handle these polymers by routine laboratory manipulations as would be employed with many ordinary solids, e.g. collecting the polymer on a filter and washing to remove by-products and unchanged products. However, the techniques described are unsatisfactory for use in a system where a colloidal suspension is employed, i.e. a latex. Reaction conditions and manipulations must be compatible for working with a colloid. The invention described herein teaches how to effect difunctional mediated couplings between a modified acrylamide latex and proteins leading to stable latex-protein products useful as diagnostic agents.

SUMMARY OF THE INVENTION

The present invention is directed to a method for chemically binding a protein having a nucleophilic functional group to a polymer particle having reactive surface hydrazide groups, said polymer particles contained in a polymer latex, by means of a difunctional compound.

The present invention further contemplates new compositions of matter consisting of the polymer particle-protein conjugates formed by the above described method.

Products derived from this invention can be used in latex agglutination tests for the detection of pregnancy or for the detection of proteins which may be indicative of disease states.

DETAILED DESCRIPTION OF THE INVENTION

The present invention is directed to a method by which proteins having a reactive group capable of forming a chemical bond with certain functional groups can be chemically bound to the surface of relatively uniform spherical polymer particles containing surface hydrazide groups in a polymer latex, through the intermediacy of difunctional compounds.

As used in the specification and claims, a "difunctional compound" is a compound having first and second functional groups which may be the same or different, with the term "first functional group" referring to a group capable of forming a chemical bond between itself and a hydrazide group on the surface of a polymer particle in a polymer latex and the term "second functional group" referring to a group capable of forming a chemical bond between itself and a reactive nucleophilic group of a protein. Preferably, the reactive nucleophilic group of the protein is a free amino group, however, depending upon the particular difunctional compound selected and the pH, other reactive groups such as guanidine, imidazole, hydroxyl, thiol, carboxyl and phenol would also be operable.

Difunctional compounds suitable for use in the present invention are well known in the art. The illustrative examples provided herein show that the known difunctional compounds glutaraldehyde, G. E. Means and R. E. Feeney, "Chemical Modification of Proteins," Holden-Day, Inc., San Francisco, 1971, pp. 40–43; 1,5-difluoro-2,4-dinitrobenzene (DFDNB), P. Cuatrecasas, S. Fuchs, and C. B. Anfinsen, J. Biol. Chem, 244, 406 (1969); 4,4'-difluoro-3,3'-dinitrodiphenyl sulfone (DFDNPS), J. S. Ram, Biochim. Biophys. Acta, 78, 228 (1963); and 2,4-dichloro-6-carboxymethylamino-s-triazine, (DCCMT), British Patent (National Research Development Corporation), 30615, July 3 (1967); 6870, Feb. 12 (1968) are suitable. Both functional groups must be capable of forming a covalent bond with either the hydrazide group on the latex particle surface or with a nucleophilic group of the protein under the reaction conditions disclosed herein. The functional groups, however, should be chemically inert to water during the reaction period.

Suitable functional group types include but are not limited to:

(a) carbonyl groups, for example, aldehydes and ketones;
(b) activated aromatic halides, for example, o- or p-nitro fluoro derivatives or dinitro fluoro derivatives;
(c) halogenated-s-triazine derivatives;
(d) epoxides;
(e) diazonium groups; and
(f) bifunctional N-hydroxysuccinimidyl esters.

A great number of difunctional compounds can be derived from these functional groups by use of varying aliphatic, aromatic, or mixtures of aliphatic or aromatic, connecting structures. Examples of preferred difunctional compounds are aliphatic dialdehydes such as glutaraldehyde and adipaldehyde; aromatic dialdehydes such as terephthalaldehyde; activated aromatic dihalide compounds such as 1,5-difluoro-2,4-dinitrobenzene and 4,4'-difluoro-3,3'-dinitrodiphenyl sulfone; halogenated-s-triazine compounds such as 2,4-dichloro-6-carboxymethylamino-s-triazine; epoxide compounds such as 1,4-butanediol diglycidyl ether; and diazonium compounds such as bisdiazobenzidine.

Proteins having reactive nucleophilic groups capable of binding with a functional group of a difunctional compound are, for example, HCG and myoglobin. However, any protein, polypeptide, or other biopolymers such as polysaccharides and polynucleotides having nucleophilic functional groups such as amino, hydroxyl, thiol or carboxyl groups capable of being coupled, as taught herein, to the described hydrazide-modified polymer particles in a polymer latex, should be suitable.

In the specification and claims, the term "hydrazide-modified latex" refers to an aqueous colloidal dispersion of a water insoluble hydrazide containing polymer. The hydrazide-modified latex can be prepared by the hydrazinolysis of an appropriate polymer latex as described in U.S. Pat. No. 4,046,723 (1977). The hydrazinolysis reaction can be performed on polymer latexes in which the latex polymer particles contain surface carboxylic amide groups. In the hydrazinolysis reaction some of the surface carboxylic amide groups are converted to carboxylic hydrazide groups. The hydrazinolysis reaction is summarized as follows:

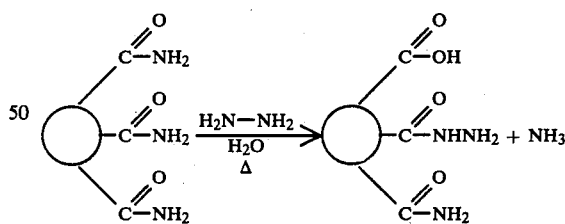

In general, the hydrazinolysis reaction is performed at a temperature of about 50° to about 80° C. for a time sufficient to obtain the desired hydrazide-modified polymer latex product, usually a reaction time of about 7 to 8 hours is sufficient. The preferred quantity of hydrazide functional groups bound to the surface of the polymer particle in the polymer latex is about 0.01 to about 0.025 milliequivalents per gram (g) of polymer solids.

Any polymer latex in which the polymer particles of the latex have surface carboxamido groups would be suitable for the hydrazinolysis reaction. For example, polymer latexes upon which the hydrazinolysis reaction can be performed to obtain the desired hydrazide-modified latex are of the type described in U.S. Pat. No. 4,094,841 (1978). Polymer latexes within the scope of the invention include those derived from styrene and acrylic acid hydrazide and those derived from styrene and other vinylcarboxamides such as methacrylamide and vinyl carboxhydrazides. Furthermore, the hydrazide-modified latex is readily obtained from esters and hydrazine latexes derived from styrene and vinyl carboxylic acid esters such as methyl, butyl, cyclohexyl, benzyl or phenyl acrylate.

Preferably the hydrazinolysis reaction is used to modify a styrene-acrylamide latex; especially preferred is a monodisperse styrene-acrylamide latex. A "monodisperse latex" is an aqueous dispersion of colloidal-size particles of the copolymer wherein the standard particle size deviation is less than 2 percent, preferably less than 1 percent. "Colloidal-size particles" as used herein refers to relatively spherical polymer particles in a polymer latex (hereinafter often referred to as latex particles) that have diameters in the range of from about 0.01 to about 2 micrometers.

Experiments illustrating the present invention were conducted using various difunctional compounds (i.e., glutaraldehyde, 1,5-difluoro-2,4-dinitrobenzene, 4,4'-difluoro-3,3'-dinitrodiphenyl sulfone and 2,4-dichloro-6-carboxymethylamino-s-triazine) and the preferred hydrazide-modified latex, i.e., a monodisperse hydrazide-modified styrene-acrylamide latex. As previously noted herein the hydrazide-modified styrene-acrylamide latex can be prepared by hydrazinolysis of a monodisperse styrene-acrylamide latex. Prior to the hydrazinolysis reaction, it was determined that the styrene-acrylamide latex starting material contained a water-soluble impurity. Subsequent experiments using styrene-acrylamide latex containing the water soluble impurity versus styrene-acrylamide latex having the water soluble impurity removed, indicated that better results are obtained when the styrene-acrylamide latex starting material has the water-soluble impurity removed prior to hydrazinolysis, and is thus the preferred methodology.

The chemical binding of the protein of the hydrazide-modified latex particles is conveniently explained by noting two distinct steps. In the first step, hereinafter called the activation step, the difunctional compound is chemically bound to the surface of the latex particle employing the conditions described herein so that a chemical reaction between one of the functional groups of the difunctional compound and a hydrazide group on the latex particle surface occurs. The activation step is illustrated for various difunctional compounds, i.e., glutaraldehyde (I), 1,5-difluoro-2,4-dinitrobenzene (II), 4,4'-difluoro-3,3'-dinitrodiphenyl sulfone (III), and 2,4-dichloro-6-carboxymethylamino-s-triazine (IV) as follows:

Step 1: Activation

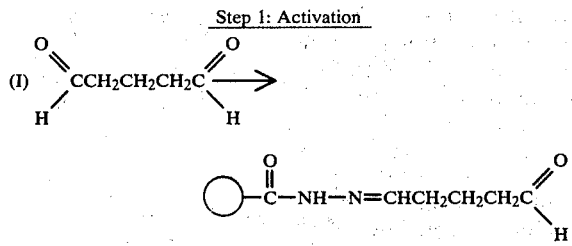

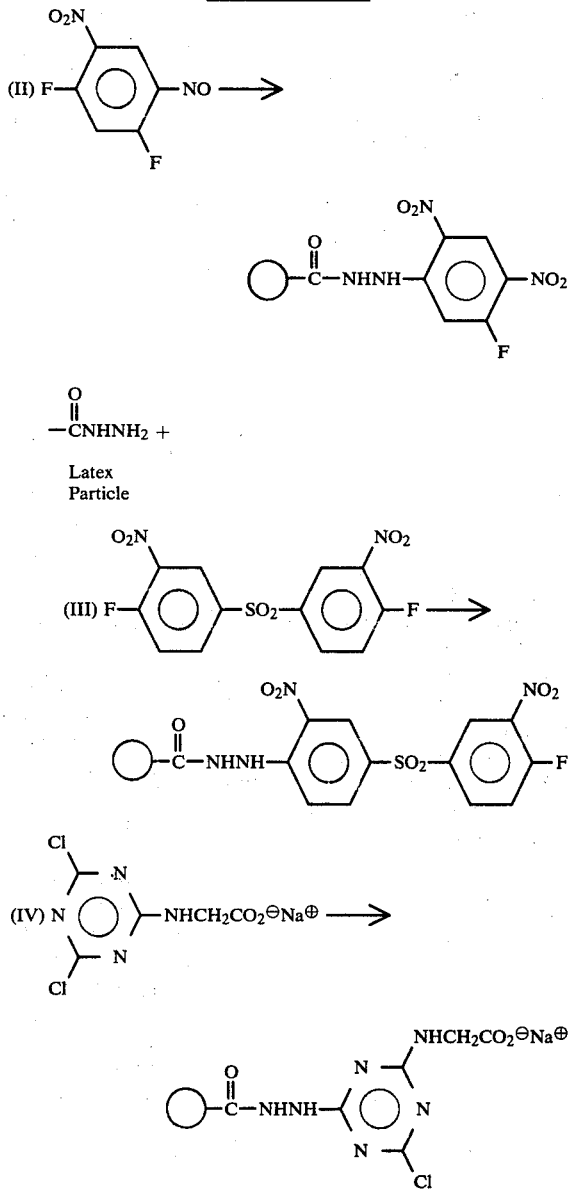

For the activation of the hydrazide-modified styrene-acrylamide latex particles, the preferred concentration of latex polymer solids is about 6 percent to about 10 percent.

In general, the activation step can be performed at room temperature (about 23° to about 26° C.), however, in certain instances a different temperature may be conveniently used and/or necessary depending upon the difunctional compound selected, as illustrated by Example 5 herein.

When the difunctional compound is glutaraldehyde the preferred reaction conditions are: a reaction temperature of about 23° to about 26° C. for about 4 hours using glutaraldehyde equivalents equal to about 80 percent to about 90 percent of the total equivalents of the functional hydrazide groups attached to the latex particle surface.

When the difunctional compound is 1,5-difluoro-2,4-dinitrobenzene the preferred reaction conditions are: a reaction temperature of about 23° to about 26° C. for about 24 hours using DFDNB equivalents equal to about 75 percent to about 90 percent of the total equivalents of the functional hydrazide groups attached to the latex particle surface. The preferred amount of solvent for DFDNB is about 10 to about 20 microliters (μl) of solvent per milligram of DFDNB. Generally an appropriate solvent for DFDNB is, for example, benzene or toluene.

A 2,4,6-Trinitrobenzenesulfonic acid (TNBS) sodium salt dihydrate (Pierce Chemical Co.) solution in water (15 mg/10 ml) was used to detect the presence of hydrazine and unsubstituted carboxylic hydrazide

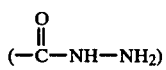

functions in polymer latexes, J. K. Inman and H. M. Dintzis, Biochemistry, 8, 4074 (1969). The former gave a magenta color and the latter a rusty-brown color with the TNBS reagent. One drop to a milliliter of the test sample was diluted with approximately 1 ml of 0.1 M sodium tetraborate (pH 9.4) and to this solution was added 1–2 drops of fresh TNBS solution; color formation was complete in several minutes.

It is sometimes desirable to add a centrifugation step after the activation step, however, the desirability of this step may depend upon the difunctional compound used. For example, it was found with glutaraldehyde that no centrifugation after activation was best, whereas with DFDNB the reverse was true.

In the second step, hereinafter called the coupling step, an aqueous buffered solution of the protein is added to the activated latex particle suspension employing conditions sufficient to obtain the desired product, such conditions may vary depending on the difunctional compound and particular protein used. In the coupling step a chemical reaction between an amino group (and presumably other reactive nucleophilic groups) of the protein and the previously non-reacted second functional group of the difunctional compound takes place.

Depending upon the particular difunctional compound selected and the pH, other reactive nucleophilic groups of the protein would also be expected to chemically react with the previously non-reacted second functional group.

For example, when the difunctional compound is glutaraldehyde, amino and guanidine groups would be the expected reactive nucleophilic groups; however, when the difunctional compound is DFDNB, reactive nucleophilic groups would include amino, guanidine, carboxyl, imidazole, phenol, hydroxyl and thiol.

Generally, aqueous buffers in the pH range of about 7 to about 8.5 which contain protein-forming salts known to the art are suitable buffers. A reaction mixture pH of from about 7 to about 8.5 is suitable for the coupling step. The resulting chemical bond between the protein and the second functional group of the difunctional compound binds the protein to the latex particles since the first functional group of the difunctional compound still binds the difunctional compound to the latex particles.

The coupling step, utilizing the hydrazide-modified latex particles (I–IV) described in the activation step, is illustrated by the following reactions:

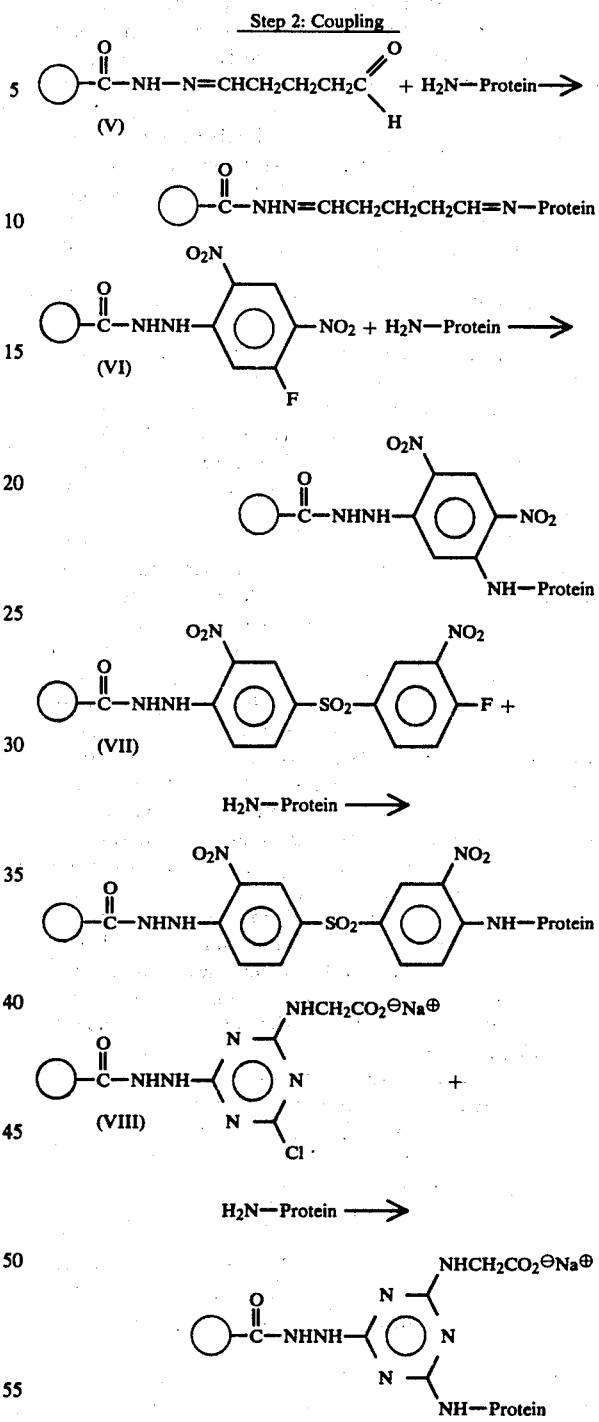

For the coupling step, the preferred quantity of hydrazide-modified styrene-acrylamide polymer particles, in a latex (activated latex polymer) is from about 3 percent to about 5 percent (weight percent) with the preferred quantity of HCG from about 14,000 to about 20,000 I.U. per gram of latex polymer solids and for human myoglobin about 3 to about 5 milligrams of human myoglobin per gram of polymer solids. Products of inferior immunological activity may result if quantities of the proteins used are below the preferred concentrations. A temperature range of about 2° to about 5° C.

for about 4 to about 7 days is preferred for the coupling reaction.

The polymer particle-protein conjugate is recovered from the reaction mixture utilizing techniques well known in the art, such as ultracentrifugation and filtration; these techniques are used primarily for the purpose of removing unreacted protein from the polymer particle-protein conjugate. Purification by ultracentrifugation to remove unchanged protein may be performed at room temperature, but the product should be stored under refrigeration at approximately 5° C.

An advantage of this invention is that residual difunctional compound can be removed from the reaction mixture after the activation step thereby avoiding unwanted crosslinking of the protein in the coupling step.

The optimum conditions to be employed in the invention may vary depending on factors such as the difunctional compound used and the protein to be bound, however, those conditions would not differ significantly from the conditions disclosed herein and are therefore readily ascertainable.

The following examples illustrate preferred embodiments of the present invention but are not to be construed as limitations thereon.

PREPARATION OF THE HYDRAZINE-MODIFIED STYRENE-ACRYLAMIDE LATEX CONTAINING WATER-SOLUBLE POLYMER IMPURITY

EXAMPLE 1

Surface amide content of styrene-acrylamide latex particles was obtained by hydrolyzing a sample of the latex with 2 equivalents of NaOH per equivalent of acrylamide in the latex polymer. The approximate composition of acrylamide in styrene-acrylamide latex polymer is 3%. The latex and caustic were heated at 97° C. to reflux for 24 hrs. The mixture was cooled, ion-exchanged with a mixed bed of DOWEX ® 50[H⊕] X8 and DOWEX ® 1[OH⊖] X8 brand resins and titrated potentiometrically with standard NaOH. The latex was found to have a particle amide content of 0.233 mequiv/g of polymer solids.

In a siliconized, 500-milliliter (ml) round-bottomed flask equipped with a condenser in the neck and a thermometer in a sidearm were placed 250 g of styrene-acrylamide latex and 25 g of 95% hydrazine. The reaction mixture was stirred and heated at 50°–55° C. for 8 hours. Following the reaction, the mixture was dialyzed (cellophane bag, approximately 3 inches in diameter) in a continuous flow cylindrical (15×40 centimeters (cm)) apparatus having a capacity of approximately 6.5 liters (l). Deionized water was directed via a tube to the bottom of the apparatus and exited at the top through an outlet tube. The flow rate was approximately one liter/hour. Continuous-flow dialysis was carried out for 4.75 days and static dialysis for another 3 days. From the above procedure, 308 g of hydrazide latex product containing 13.8% polymer solids was obtained. Total carboxyl and hydrazide functions were determined using a method similar to that described in the hereinabove cited Inman and Dintzis article. The latex particle was found to have the following surface composition noted in milliequivalents (mequiv) per gram of polymer solid followed by the percentage of the surface composition represented by the noted functionality:

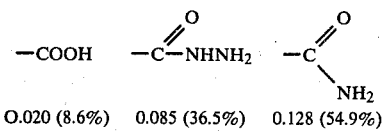

0.020 (8.6%)   0.085 (36.5%)   0.128 (54.9%)

To assure complete removal of hydrazine, a 75 g portion of the hydrazine-modified latex was placed in an 8-ounce (oz) polyethylene bottle and treated with a mixed bed of ion exchange resins (Dowex ® 50 [H⊕] X8, 2 g (about 3.8 mequiv) and Dowex ® 1 [OH⊖] X8, 2 g (about 3 mequiv)) of 30–50 mesh. The bottle was capped and rolled gently to mix the contents at intervals of approximately 10 minutes for a period of 2 hours. After settling, the latex was decanted and filtered through a mat of glass wool. There was recovered 66.9 g of product containing 13.6% polymer solids.

PREPARATION OF THE HYDRAZIDE-MODIFIED STYRENE-ACRYLAMIDE LATEX FREE OF WATER-SOLUBLE IMPURITY

Example 2

Approximately 175 g of styrene-acrylamide latex was centrifuged twice at 12,000 r.p.m. The latex was reconstituted each time with distilled water and finally filtered by gravity through a varnish filter (approximately 80–100 mesh). There was recovered 163 g of latex containing 12.1% polymer solids. The latex particle was found to have a surface amide content of 0.058 mequiv/g polymer solids.

A mixture of 150 g of this water-soluble polymer-free styrene-acrylamide latex and 15 g of 95% hydrazine was heated at 58°–60° C. as described previously for 7 hours. The crude reaction mixture was dialyzed in the continuous-flow apparatus for 3 days, transferred to a fresh dialysis bag and further dialyzed against 6 liters of water at intervals of 3, 1 and 1 days. Appearance of hydrazine in the baths was followed by using the TNBS reagent and 1 ml bath samples. Response to TNBS reagent in the last bath was weak. The dialyzed latex product, 280 g, was further treated with 6 g (approximately 11.4 mequiv) of Dowex ® 50 [H⊖] X8 (30–50 mesh) brand resin for 2 hours and further prepared as described in Example 1. There was recovered 278 g of impurity-free hydrazide-modified styrene-acrylamide latex having 6.06% polymer solids. The latex particle was found to have the following surface composition (mequiv per gram of polymer solids):

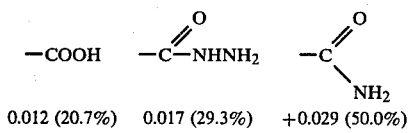

0.012 (20.7%)   0.017 (29.3%)   +0.029 (50.0%)

COUPLING AND ADSORPTION REACTIONS OF HCG WITH HYDRAZIDE-MODIFIED STYRENE-ACRYLAMIDE LATEX CONTAINING WATER-SOLUBLE POLYMER IMPURITY

Human Chorionic Gonadotropin (HCG) Protein

Example 3—Glutaraldehyde Coupling

A mixture of 5.0 g (0.68 g polymer; 0.058 mequiv hydrazide) of hydrazide-modified styrene-acrylamide latex of Example 1, 3 ml of distilled water and 1.7 ml (5.1 mg; 0.051 mequiv) of glutaraldehyde solution (3 mg/ml) was stirred at room temperature for 4 hours. A test with the TNBS reagent and 2 drops of the reaction mixture indicated that most of the hydrazide groups had reacted. To the activated latex mixture was added a solution of 10,000 I.U. of HCG in phosphate-saline buffer No. 1.

The HCG used throughout the examples was isolated from human urine and was obtained from Sigma Chemical Co. The HCG preparation was lyophilized and contained in septum bottles having 5,000 international units (I.U.) of HCG, 50 mg of mannitol, and sodium phosphate buffer such that solution in 10 ml of water gave a pH of 7.2. Phosphate-saline buffer No. 1 was prepared by diluting 3.68 ml of 0.5 M $KH_2PO_4$, 32.2 ml of 0.5 M $Na_2HPO_4$, 5.84 g of NaCl and 10 ml of 1% Merthiolate ® to 1 liter with deionized water, which gave a phosphate-saline buffer with a pH of 8.0 at 5° C. After stirring 5 days at 5° C. the reaction mixture was diluted 1-fold with buffer and centrifuged for 30 minutes at 20,000 r.p.m. (32,000 times gravity) at 5° C. The supernatant was removed carefully and the latex polymer residue was resuspended in buffer with the aid of a siliconized, smooth, round-tipped glass rod and centrifuged again. After resuspension in phosphate-saline buffer No. 1, the mixture was filtered by gravity through a thin mat of glass wool supported in a small polyethylene funnel. The funnel was rinsed with a little buffer and the rinse was added to the filtrate. There was obtained 26.6 g of latex-HCG product.

Example 4—1,5-Difluoro-2,4-dinitrobenzene Coupling

A mixture of 5.0 g (0.68 g polymer; 0.058 mequiv hydrazide) of hydrazide-modified styrene-acrylamide latex of Example 1 and 5 ml of distilled water was stirred in a siliconized, 25-ml round-bottomed flask. To this briskly stirred mixture was added a solution of 10.0 mg (0.049 mequiv) of 1,5-difluoro-2,4-dinitrobenzene (DFDNB) in 100 µl of benzene with the aid of a 50-µl pipette. The DFDNB solution vial and pipette were rinsed with 20 µl of benzene and the rinse was also added to the reaction mixture. Stirring at room temperature was continued for approximately 23 hours followed by centrifugation for 30 minutes at 20,000 r.p.m. at 5° C. After removal of the supernatant, the latex polymer residue was redispersed in 9 ml of water and treated with a solution of 10,000 I.U. of HCG in 8 ml of phosphate-saline buffer No. 1. The reaction mixture was stirred at approximately 5° C. for 5 days, followed by centrifugation in the same manner as described in Example 3, yielding 26.6 g of light yellow colored latex-HCG product.

Example 5—4,4'-Difluoro-3,3'-dinitrodiphenyl sulfone Coupling

To a stirred mixture of 2.5 g of hydrazide-modified styrene-acrylamide latex (0.34 g polymer; 0.029 mequiv hydrazide) of Example 1 and 2.5 ml of water in a siliconized 25-ml round-bottomed flask was added a solution of 8.59 mg (0.025 mequiv) of 4,4'-difluoro-3,3'-dinitrodiphenyl sulfone (Pierce Chemical Co.) in 100 µl of nitromethane. An additional 25 µl of nitromethane was used as rinse. The resulting mixture was stirred at 50°–55° C. for 5.5 hrs, cooled to room temperature and then filtered carefully through a coarse sintered glass funnel using a low vacuum. The combined filtrate and rinse (1 ml) was treated with a solution of 5,000 I.U. of HCG in 3 ml of phosphate-saline buffer No. 1 and the resulting mixture was stirred at approximately 5° C. for 5 days. The reaction mixture was worked up by centrifugation as described in Example 3. There was obtained 13.3 g of very pale yellow latex-HCG product.

Example 6—2,4-Dichloro-6-carboxymethylamino-s-triazine Coupling

A stirred mixture of 2.5 g (0.34 g polymer; 0.029 mequiv of hydrazide) of hydrazide-modified styrene-acrylamide latex of Example 1 and 2.5 ml of distilled water was treated with a solution of 5.28 mg (0.022 mequiv) of 2,4-dichloro-6-carboxymethylamino-s-triazine hydrate in 0.3 ml of 0.1 M $NaHCO_3$ and stirred at room temperature for 3 hours. The mixture was diluted with an equal volume of 0.05 M $NaHCO_3$ solution and centrifuged for 35 minutes at 20,000 r.p.m. at 5° C. The supernatant was discarded and the latex polymer residue was resuspended in a solution of 5,000 I.U. of HCG in 8 ml of phosphate-saline buffer No. 1 and stirred at approximately 5° C. for 7 days. The reaction was worked up by centrifugation as described in Example 3 yielding 12.1 g of latex-HCG product.

Example 7—Adsorption

A mixture of 3.0 g (0.34 g polymer; 0.026 mequiv hydrazide) of hydrazide-modified styrene-acrylamide latex, 2 ml of distilled water and a solution of 5,000 I.U. of HCG in 3.5 ml of phosphate-saline buffer No. 1 were stirred at approximately 5° C. for 5 days whereupon the reaction mixture was further prepared by centrifugation as described in Example 3, yielding 13.3 g of latex-HCG adsorption product.

COUPLING REACTION OF HUMAN MYOGLOBIN (Hmb) WITH HYDRAZIDE-MODIFIED STYRENE-ACRYLAMIDE LATEX CONTAINING WATER-SOLUBLE POLYMER IMPURITY

Example 8—1,5-Difluoro-2,4-dinitrobenzene Coupling

A mixture of 1.67 g (0.23 g polymer; 0.019 mequiv hydrazide) of hydrazide-modified styrene-acrylamide latex of Example 1 and 1.7 ml of distilled water was stirred in a siliconized, 25-ml round-bottomed flask. To this briskly stirred mixture was added a solution of 3.40 mg (0.0167 mequiv) of DFDNB in 40 µl of benzene; additional benzene, 15 µl, was used for rinsing. After stirring at room temperature for 23 hours, the reaction mixture was diluted with water to 12 g and centrifuged at 20,000 r.p.m. at 5° C. The supernatant was discarded and the latex polymer residue was resuspended in 2 ml of cold distilled water. To this suspension was added a solution of 1 ml (2.4–4.8 mg) of skeletal human myoglobin in 5 ml of phosphate-saline buffer No. 1 and the resulting mixture was stirred for 4.8 days. Skeletal human myoglobin was obtained from Bio-Science Labs; having a concentration of 2.4–4.8 mg of skeletal human myoglobin per milliliter obtained frozen in 1-ml portions in pH 7.2 phosphate buffer (Ionic strength=0.01 M) saline solution. The reaction mixture was then prepared as in previous examples, using phosphate-saline buffer No. 1, which gave a yield of 11.6 g of pale yellow latex-Hmb product.

COUPLING AND ADSORPTION REACTIONS OF HCG WITH HYDRAZIDE-MODIFIED STYRENE-ACRYLAMIDE LATEX FREE OF WATER-SOLUBLE POLYMER IMPURITY

Example 9—Glutaraldehyde Coupling

Hydrazide-modified styrene-acrylamide latex of Example 2, 11.2 g (0.68 g polymer; 0.012 mequiv hydrazide) was concentrated to 6.5 g by centrifugation and distilled water reconstitution. To this was added 0.21 ml (1.0 mg; 0.010 mequiv) of glutaraldehyde solution (4.76 mg/ml) and the mixture was stirred for 4 hours. The TNBS test reagent showed that most of the hydrazide groups had reacted. To this mixture was added a solution of 10,000 I.U. of HCG in 7 ml of phosphate-saline buffer No. 1 and the reaction mixture was stirred 5 days at approximately 5° C., followed by centrifugation at 15,000 r.p.m. (27,000 times gravity) in the usual manner, and 26.6 g of latex-HCG product obtained.

EXAMPLE 10—1,5-Difluoro-2,4-dinitrobenzene Coupling

A 11.2 g (0.68 g polymer; 0.012 mequiv hydrazide) portion of hydrazide-modified styrene-acrylamide latex of Example 2 was concentrated to 10 g as described in Example 9. The latex was activated with a solution of 2.0 mg (0.01 mequiv) of DFDNB in 100 µl of benzene (20 µl of additional benzene was used for rinsing) in the same manner as described in Example 4. The activated latex was then coupled with 10,000 I.U. of HCG dissolved in 7 ml of phosphate-saline buffer No. 1 and the product obtained essentially as described in Example 4. There was obtained 26.6 g of pale yellow colored latex-HCG product.

Example 11—Adsorption

Hydrazide-modified styrene-acrylamide latex of Example 2, 5.6 g (0.34 g polymer; 0.006 mequiv hydrazide), was concentrated to approximately 5 g by centrifugation and reconstituted with distilled water as described in Example 9. The reconstituted latex was then treated with 5,000 I.U. of HCG in 3.5 ml of phosphate-saline buffer No. 1 and the absorption reaction carried out and the product obtained essentially as described in Example 7. There was obtained 13.3 g of latex-HCG adsorption product.

COUPLING AND ADSORPTION REACTIONS OF HUMAN MYOGLOBIN WITH HYDRAZIDE-MODIFIED STYRENE-ACRYLAMIDE LATEX FREE OF WATER-SOLUBLE POLYMER IMPURITY

Example 12—1,5-Difluoro-2,4-dinitrobenzene Coupling

The activation step of this example was carried out as described in Example 4 using 3.8 g (0.23 g polymer; 0.004 mequiv hydrazide) of hydrazide-modified styrene-acrylamide latex of Example 2 and 0.61 mg (0.003 mequiv) of DFDNB dissolved in approximately 20 µl of benzene with approximately 5 µl of benzene for rinsing.

After activation the reaction mixture was diluted to 15.3 g and centrifuged at 15,000 r.p.m. at 5° C. for 30 minutes. The latex was reconstituted with 3 ml of water and to this stirred mixture was added two 0.25-ml portions (0.89 mg) of human cardiac myoglobin solution and 3 ml of sterile saline (diluent and rinse for the transfer of the myoglobin solution). The reaction mixture was further diluted with 4.5 ml of phosphate-saline buffer No. 2, (prepared by diluting 6.22 ml of 0.5 M $KH_2PO_4$, 64.6 ml of 0.5 M $Na_2HPO_4$, 8.5 g of NaCl and 10 ml of 1% Merthiolate ® to 1 liter with deionized water, giving a phosphate-saline buffer with a pH of 7.9 at 5° C.), stirred for 6 days at approximately 5° C., filtered through a thin mat of glass wool followed by centrifugation as described in Example 4 using phosphate-saline buffer No. 1. There was obtained 10.2 g of very pale yellow latex-myoglobin product.

Example 13—Adsorption

A mixture of 3.8 g (0.23 g; approximately 0.004 mequiv hydrazide) of hydrazide-modified styrene-acrylamide latex, two 0.25-ml portions (0.89 mg) of human cardiac myoglobin solution, 3 ml of sterile saline and 4.5 ml of phosphate-saline buffer No. 2 were stirred at approximately 5° C. for 6 days. The reaction mixture was further prepared as described in Example 12. There was obtained 11.0 g of latex-myoglobin product.

The latex-protein products of the previous examples were immunologically evaluated by Agglutination Slide Testing utilizing the following procedure:

A triple-well, black, opaque glass slide (50×111×ca 0.5 mm) was used in the agglutination slide tests. All reagents and latexes were brought to room temperature. Aliquots of 25-µl each of phosphate-saline buffer No. 1 and antiserum solution were mixed on the slide with a small wooden stick. The latex-protein preparation, 25 µl, was applied to the slide and mixed well with antiserum and buffer; the slide was then gently rocked in and out of a horizontal plane. Agglutination was noted within two minutes and recorded based on a 0-4+ scale. Control or base values for agglutination in the absence of antiserum were determined by conducting a test with two parts of buffer and one part of latex-protein preparation. The reciprocal antiserum dilution endpoint (RADE) titers for agglutination of the latex-protein products were determined and are summarized in Table I for the Latex-HCG products and Table II for the Latex-Human Myoglobin products.

Goat anti-human myoglobin serum was obtained from Miles Laboratory. Myoglobin, purified from human pathological urine, was used as the antigen in the preparation of this antiserum. Two milliliters of lyophilized antiserum was diluted to 20 ml with phosphate-saline buffer No. 1 giving a solution of approximate titer 1/10.

Rabbit anti-human chorionic gonadotropin serum was obtained from Miles Laboratory.

TABLE I

Immunological Agglutination Slide Test Data of Hydrazide-Modified Styrene-Acrylamide Latex-HCG Products

| Latex-HCG Product of Example | Coupling Agent | Water-Soluble Polymer Impurity Present in Starting Latex | Reciprocal Antiserum Dilution Endpoint Titer |
|---|---|---|---|
| 3 | Glutaraldehyde | Yes | 320 |
| 9 | Glutaraldehyde | No | 320 |
| 4 | DFDNB | Yes | 320 |
| 10 | DFDNB | No | 960 |
| 5 | DFDNPS | Yes | 160 |
| 6 | DCCMT | Yes | 160 |
| 7 | Adsorption | Yes | ≦20 |
| 11 | Adsorption | No | 160 |

All products in Table I had control or base agglutination values of 0 and agglutination ratings of ≧2+. Lyophilized Pentex ® (Miles Laboratory) rabbit anti-human chorionic gonadotropin serum Lot 13 diluted serially with phosphate-saline buffer No. 1 was used.

Example 7 is a control example wherein the hydrazide-modified styrene-acrylamide latex containing water-soluble impurity was mixed with HCG under standard test conditions but without the use of a difunctional compound, thereby producing a latex-HCG adsorption product. Example 11 is the same as Example 7 except that this control uses a hydrazide-modified styrene-acrylamide latex free of water-soluble impurity.

Table I indicates that, in general, hydrazide-modified styrene-acrylamide latex free of water-soluble polymer impurity yields latex-HCG products with equivalent or greater immunological activity than the corresponding products derived from latex containing the impurity. Table I also shows that 1,5-difluoro-2,4-dinitrobenzene is superior to glutaraldehyde as a difunctional coupling agent, that either 1,5-difluoro-2,4-dinitrobenzene or glutaraldehyde is superior to 4,4'-difluoro-3,3'-dinitrodiphenyl sulfone or 2,4-dichloro-6-carboxymethylamino-s-triazine as a difunctional coupling agent and that the chemical binding of HCG to hydrazide-modified styrene-acrylamide latex by means of a difunctional compound leads to more immunologically active products than adsorption.

TABLE II

Immunological Agglutination Slide Test Data of Hydrazide-Modified Styrene-Acrylamide Latex-Human Myoglobin Products

| Latex-Human Myoglobin Product of Example | Coupling Agent | Water-Soluble Polymer Impurity Present in Starting Latex | Reciprocal Antiserum Dilution Endpoint Titer | | Agglutination Rating |
|---|---|---|---|---|---|
| | | | Control | Test | |
| 8 | DFDNB | Yes | 0 | 10 | 1-2+ |
| 12 | DFDNB | No | 0 | 40 | 2-3+ |
| | | | | 80 | 1-2+ |
| 13 | Adsorption | No | 1+ | 80 | 2+ |

In Table II, Example 13 is the control example wherein the hydrazide-modified styrene-acrylamide latex free of water-soluble impurity is mixed with human myoglobin under standard conditions in the absence of a difunctional compound, thereby producing a latex-human myoglobin adsorption product.

Table II indicates that DFDNB coupling of human myoglobin to hydrazide-modified styrene-acrylamide latex in the absence of water-soluble polymer impurity produces more immunologically active products. Table II also shows that adsorption may yield a latex-human myoglobin product comparable to the chemically coupled latex-human myoglobin product. Nonetheless, chemical coupling would be preferred for the reasons cited in U.S. Pat. No. 3,853,987 (1974) and 3,856,931 (1974).

The latex embodied in this invention has an advantage over other latexes presently used as diagnostic agents. The advantage is that the latex particles are monodisperse or uniform in size whereas other diagnostic latexes commonly used, U.S. Pat. No. 3,856,931 (1974), have a distribution of sizes. Uniformity of size assures an equal statistical distribution of antigen or antibody molecules on the latex particles' surfaces. For a given weight of polymer, the surface area of the latex will increase with a decrease in the size of the particles and vice versa. Thus, in a latex having different particle sizes the smaller particles will have a greater surface area and consequently more total reaction sites than the larger particles. Therefore, an unequal distribution of antigen or antibody on the latex particles will lead to unequal agglutination of particles and poorly defined diagnostic results.

What is claimed is:

1. A method for coupling in a polymer latex a protein having at least one reactive nucleophilic group to polymer particles containing reactive surface hydrazide groups, said polymer particles having reactive surface hydrazide groups derived from styrenic polymer particles containing surface carboxamido groups, by using a difunctional compound having first and second functional groups, so that a polymer particle-protein conjugate is obtained, which method comprises:
   (1) forming a first chemical bond between said first functional group and a reactive surface hydrazide group of the polymer particle in the latex; and
   (2) forming a second chemical bond between said second functional group and a reactive nucleophilic group of the protein at a pH of about 7 to about 8.5 for a time sufficient to form the second chemical bond; and
   (3) recovering the polymer particle-protein conjugate.

2. The method of claim 1 wherein the hydrazide-modified polymer latex is a monodisperse polymer latex.

3. The method of claim 1 wherein the protein is human chorionic gonadotropin.

4. The method of claim 1 wherein the protein is human myoglobin.

5. The polymer particle-protein conjugate formed by the method of claim 1.

6. The method of claim 1 wherein the polymer latex is a hydrazide-modified styrene-acrylamide latex having average particle diameters of about 0.01 to about 2 micrometers.

7. The method of claim 6 wherein the hydrazide-modified styrene-acrylamide latex is a monodisperse hydrazide-modified styrene-acrylamide latex.

8. The method of claim 6 wherein the protein is human chorionic gonadotropin and the quantity of human chorionic gonadotropin is about 14,000 to about 20,000 International Units per gram of polymer solids.

9. The method of claim 6 wherein the protein is human myoglobin and the quantity of human myoglobin is about 3 to about 5 milligrams per gram of polymer solids.

10. The polymer particle-protein conjugate formed by the method of claim 6.

11. The polymer particle-protein conjugate of claim 10 wherein the protein is human chorionic gonadotropin.

12. The polymer particle-protein conjugate of claim 10 wherein the protein is human myoglobin.

* * * * *

UNITED STATES PATENT AND TRADEMARK OFFICE
CERTIFICATE OF CORRECTION

PATENT NO. : 4,421,896
DATED : December 20, 1983
INVENTOR(S) : Linneaus C. Dorman It is certified that error appears in the above—identified patent and that said Letters Patent is hereby corrected as shown below:

First page, second column, under title OTHER PUBLICATIONS, line 6, "Poteins," should read --Proteins,--.

Column 1, line 54, "pregnancy," should read --pregnancy.--.

Column 1, line 59, "tests:" should read --testis.--.

Column 5, line 43, "protein of the" should read --protein to the--.

Column 6, line 19, formula " $-\overset{\overset{O}{\|}}{C}NHNH_2+$ " should read

--  --.

Column 10, line 47, "[H⊖]" should read --[H$^\oplus$]--.

Column 10, line 60, "+0.029(50.0%)" should read --0.029(50.0%)--.

Signed and Sealed this

Twenty-fourth Day of April 1984

[SEAL]

Attest:

GERALD J. MOSSINGHOFF

Attesting Officer    Commissioner of Patents and Trademarks